United States Patent
Tkaczyk et al.

(10) Patent No.: US 10,779,791 B2
(45) Date of Patent: Sep. 22, 2020

(54) SYSTEM AND METHOD FOR MOBILE X-RAY IMAGING

(71) Applicant: GENERAL ELECTRIC COMPANY, Schenectady, NY (US)

(72) Inventors: John Eric Tkaczyk, Delanson, NY (US); David Allen Langan, Clifton Park, NY (US); Peter William Lorraine, Niskayuna, NY (US); Biju Jacob, Niskayuna, NY (US); Feng Pan, Clifton Park, NY (US); Hao Lai, Rexford, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 172 days.

(21) Appl. No.: 15/923,497

(22) Filed: Mar. 16, 2018

(65) Prior Publication Data
US 2019/0282194 A1 Sep. 19, 2019

(51) Int. Cl.
A61B 6/00 (2006.01)

(52) U.S. Cl.
CPC ............ *A61B 6/542* (2013.01); *A61B 6/4028* (2013.01); *A61B 6/4405* (2013.01); *A61B 6/5294* (2013.01)

(58) Field of Classification Search
CPC ..... A61B 6/542; A61B 6/4028; A61B 6/4405; A61B 6/5294
USPC ................................ 378/95, 62, 4, 108, 205
See application file for complete search history.

(56) References Cited

U.S. PATENT DOCUMENTS

| | | | | |
|---|---|---|---|---|
| 4,185,198 A | * | 1/1980 | Fujimoto | H05G 1/64 378/116 |
| 4,349,917 A | * | 9/1982 | Moore | A61B 6/4283 378/164 |
| 5,233,639 A | * | 8/1993 | Marks | H05G 1/60 378/42 |
| 5,400,378 A | * | 3/1995 | Toth | A61B 6/032 378/108 |
| 5,432,339 A | * | 7/1995 | Gordon | G01D 5/24452 250/231.13 |

(Continued)

FOREIGN PATENT DOCUMENTS

JP 2008178714 A 8/2008

OTHER PUBLICATIONS

Wj et al., "ROI-Based Image Registration for Digital Subtraction Radiography", Oral Surg Oral Med Oral Pathol Oral Radiol Endod., https://www.ncbi.nlm.nih.gov/pubmed/16545718, vol. 101, Issue 04, pp. 523-529, Apr. 2006.

(Continued)

*Primary Examiner* — Blake C Riddick
(74) *Attorney, Agent, or Firm* — Fletcher Yoder, P.C.

(57) ABSTRACT

A method for X-ray imaging includes determining one or more pre-shot parameters corresponding to a region of interest in a subject based on an optical image of the region of interest obtained from an optical sensor. The method further includes controlling an X-ray device to generate a pre-shot X-ray image using a first X-ray dosage, based on the one or more-pre-shot parameters. The method also includes determining at least one main-shot parameter based on the pre-shot X-ray image. The method includes controlling the X-ray device to generate a main-shot X-ray image using a second X-ray dosage greater than the first X-ray dosage, based on the at least one main-shot parameter.

18 Claims, 3 Drawing Sheets

(56) References Cited

U.S. PATENT DOCUMENTS

| | | | |
|---|---|---|---|
| 5,450,462 A * | 9/1995 | Toth | A61B 6/032 378/108 |
| 6,222,902 B1 | 4/2001 | Lin | |
| 6,222,907 B1 * | 4/2001 | Gordon, III | A61B 6/4225 378/116 |
| 6,285,739 B1 * | 9/2001 | Rudin | A61B 6/4233 378/62 |
| 6,393,090 B1 * | 5/2002 | Hsieh | G01N 23/06 378/4 |
| 6,795,526 B2 | 9/2004 | Walker et al. | |
| 6,816,572 B2 * | 11/2004 | Jabri | A61B 6/4035 378/98.12 |
| 7,292,675 B1 * | 11/2007 | Li | A61B 6/025 378/116 |
| 7,295,691 B2 * | 11/2007 | Uppaluri | A61B 6/482 382/130 |
| 8,454,235 B2 * | 6/2013 | Sawada | G01T 1/2014 378/205 |
| 9,615,803 B2 | 4/2017 | Zou et al. | |
| 2001/0031033 A1 * | 10/2001 | Toth | A61B 6/032 378/19 |
| 2002/0075997 A1 * | 6/2002 | Unger | A61B 6/405 378/98.9 |
| 2002/0085672 A1 * | 7/2002 | Ganin | A61B 6/00 378/108 |
| 2003/0081734 A1 * | 5/2003 | Nicolas | A61B 6/0457 378/205 |
| 2003/0165216 A1 * | 9/2003 | Walker | A61B 6/00 378/108 |
| 2004/0101087 A1 * | 5/2004 | Hsieh | A61B 6/032 378/4 |
| 2004/0247069 A1 * | 12/2004 | Arai | A61B 6/469 378/4 |
| 2005/0006586 A1 * | 1/2005 | Balan | A61B 6/5235 250/363.02 |
| 2005/0133706 A1 * | 6/2005 | Eberhard | A61B 6/025 250/234 |
| 2005/0133708 A1 * | 6/2005 | Eberhard | A61B 6/025 250/234 |
| 2005/0135558 A1 * | 6/2005 | Claus | A61B 6/02 378/42 |
| 2005/0226375 A1 * | 10/2005 | Eberhard | A61B 6/482 378/62 |
| 2005/0267348 A1 * | 12/2005 | Wollenweber | A61B 6/544 600/407 |
| 2006/0262904 A1 * | 11/2006 | Mertelmeier | A61B 6/02 378/62 |
| 2007/0036272 A1 * | 2/2007 | Johansson | A61B 6/488 378/108 |
| 2007/0076928 A1 * | 4/2007 | Claus | G06T 11/006 382/128 |
| 2007/0297569 A1 | 12/2007 | Saunders | |
| 2008/0037708 A1 * | 2/2008 | Kuzmanovic | A61B 6/08 378/62 |
| 2008/0118130 A1 * | 5/2008 | Pillai | G16H 10/60 382/131 |
| 2008/0137806 A1 * | 6/2008 | Chang | A61B 6/037 378/17 |
| 2009/0161816 A1 * | 6/2009 | De Man | A61B 6/4028 378/9 |
| 2009/0168951 A1 * | 7/2009 | Yan | A61B 6/032 378/8 |
| 2010/0027742 A1 * | 2/2010 | Movassaghi | A61B 6/544 378/62 |
| 2010/0067650 A1 * | 3/2010 | Arai | A61B 6/544 378/16 |
| 2010/0111395 A1 * | 5/2010 | Tamakoshi | G06T 7/0012 382/132 |
| 2011/0075793 A1 | 3/2011 | Akahori et al. | |
| 2011/0150175 A1 * | 6/2011 | Hsieh | A61B 6/4021 378/16 |
| 2011/0305320 A1 * | 12/2011 | Suuronen | A61B 6/467 378/98.5 |
| 2012/0020451 A1 * | 1/2012 | Nukui | A61B 6/488 378/4 |
| 2012/0051498 A1 * | 3/2012 | Koishi | A61B 6/025 378/10 |
| 2012/0051500 A1 * | 3/2012 | Johansson | A61B 6/025 378/22 |
| 2012/0063566 A1 * | 3/2012 | Smith | A61B 6/502 378/37 |
| 2012/0128125 A1 | 5/2012 | Jabri et al. | |
| 2012/0155609 A1 * | 6/2012 | Lemminger | A61B 6/032 378/62 |
| 2012/0300910 A1 * | 11/2012 | Gorges | A61B 6/589 378/198 |
| 2013/0301799 A1 * | 11/2013 | Kang | A61B 6/5258 378/62 |
| 2014/0064444 A1 * | 3/2014 | Oh | A61B 6/482 378/37 |
| 2014/0072100 A1 | 3/2014 | Jang et al. | |
| 2014/0112434 A1 | 4/2014 | Jang et al. | |
| 2014/0119507 A1 * | 5/2014 | Oh | A61B 6/52 378/62 |
| 2014/0133626 A1 * | 5/2014 | Jang | A61B 6/542 378/62 |
| 2014/0185762 A1 * | 7/2014 | Lee | G01N 23/04 378/62 |
| 2014/0254757 A1 * | 9/2014 | Oh | A61B 6/484 378/62 |
| 2014/0355735 A1 * | 12/2014 | Choi | A61B 6/5223 378/8 |
| 2014/0369472 A1 * | 12/2014 | Oh | A61B 6/484 378/62 |
| 2015/0063545 A1 * | 3/2015 | Lee | A61B 6/545 378/91 |
| 2015/0078508 A1 * | 3/2015 | Lee | A61B 6/542 378/4 |
| 2015/0150528 A1 * | 6/2015 | Kim | A61B 6/5205 378/37 |
| 2015/0228071 A1 * | 8/2015 | Jockel | A61B 6/08 382/132 |
| 2015/0245806 A1 * | 9/2015 | Kim | B25J 9/1694 378/37 |
| 2015/0359498 A1 * | 12/2015 | Zou | A61B 6/469 378/62 |
| 2015/0359502 A1 * | 12/2015 | Zou | A61B 6/5217 378/62 |
| 2015/0374314 A1 | 12/2015 | Maack et al. | |
| 2016/0078619 A1 * | 3/2016 | Hsieh | A61B 6/5252 378/4 |
| 2016/0081635 A1 * | 3/2016 | Divine | A61B 6/488 378/19 |
| 2016/0157799 A1 * | 6/2016 | Lee | A61B 6/463 378/5 |
| 2016/0183896 A1 * | 6/2016 | Muller | A61B 6/481 600/424 |
| 2016/0256128 A1 * | 9/2016 | Wang | A61B 6/54 |
| 2017/0000445 A1 * | 1/2017 | Beak | A61B 6/4233 |
| 2017/0143292 A1 * | 5/2017 | Yun | A61B 6/032 |
| 2017/0143293 A1 | 5/2017 | Park et al. | |
| 2017/0201708 A1 * | 7/2017 | Igarashi | G06F 3/048 |
| 2017/0281107 A1 * | 10/2017 | Park | A61B 6/542 |
| 2019/0209117 A1 * | 7/2019 | Duewer | A61B 6/145 |

OTHER PUBLICATIONS

Guo et al., "Content Based Image Retrieval From Chest Radiography Databases", Conference Record of the Forty-Third Asilomar Signals, Systems and Computers, http://ieeexplore.ieee.org/document/5470194/, Nov. 1-4, 2009.

Kasban et al., "Automatic Segmentation of Industrial Radiographic Images", Computer Engineering & Systems (ICCES), http://ieeexplore.ieee.org/document/6141045/, Nov. 29-Dec. 1, 2011.

(56) References Cited

OTHER PUBLICATIONS

International Search Report and Written Opinion, PCT/US2019/022541, dated Jun. 24, 2019 (11 pages).

\* cited by examiner

SYSTEM AND METHOD FOR MOBILE X-RAY IMAGING

BACKGROUND

Embodiments of the present specification relate generally to mobile X-ray devices, and more particularly to a system and a method for minimizing exposure of a subject to X-ray radiations during an optimal X-ray imaging.

A typical radiography system uses X-rays attenuated by a subject to impact a film or a digital X-ray detector to generate an X-ray image. During medical diagnosis, such a radiography system is used to visualize internal tissues and diagnose patient ailments. The X-ray system uses a digital X-ray detector for generating electrical signals indicative of received X-ray beams and employs digital processing techniques for generating an X-ray image.

Mobile X-ray systems are very versatile for performing imaging operations of patients in a critical condition and lesser mobility. Portable digital X-ray detectors may be used for both mobile or stationary X-ray systems to receive power and communicate imaging data via a cable to other components, such as a computer or an image processor. In other instances, battery-powered, wireless digital X-ray detectors may be used instead of wired digital X-ray detectors. Conventional X-ray systems require well-trained technicians to operate the systems. An imaging workflow is largely a manual operation where an operator initializes a period of exposure of a patient to X-ray radiations after positioning a X-ray source and a X-ray detector relative to the patient. Inaccuracies related to visual estimation of an operator and/or patient motion occurring after positioning the X-ray source and the X-ray detector can result in generation of unacceptable images due to an image of an anatomy missing with reference to projected field of view of the X-ray system. If an anti-scatter grid is present in the X-ray detector, degraded X-ray images may be generated due to misalignment of the anti-scatter grid with an X-ray beam generated from the X-ray source. Manual adjustment of a mobile X-ray source and a portable X-ray detector may result in generation of degraded X-ray images. Generation of unacceptable images due to positioning inaccuracies and incorrect choice of X-ray imaging parameters can result in repeated cycles of the imaging process and prolonged exposure of a subject to X-ray radiations.

BRIEF DESCRIPTION

In accordance with one aspect of the present specification, a method for X-ray imaging is disclosed. The method includes determining one or more pre-shot parameters corresponding to a region of interest in a subject based on an optical image of the region of interest obtained from an optical sensor. The method further includes controlling an X-ray device to generate a pre-shot X-ray image using a first X-ray dosage, based on the one or more-pre-shot parameters. The method also includes determining at least one main-shot parameter based on the pre-shot X-ray image. The method includes controlling the X-ray device to generate a main-shot X-ray image using a second X-ray dosage greater than the first X-ray dosage, based on the at least one main-shot parameter.

In accordance with another aspect of the present specification, a mobile X-ray imaging system is disclosed. The system includes an optical sensor configured to obtain an optical image of a region of interest in a subject. The system further includes an x-ray device configured to generate a pre-shot X-ray image, using a first X-ray dosage, based on one or more pre-shot parameters. The X-ray device is further configured to generate a main-shot X-ray image, using a second X-ray dosage greater than the first X-ray dosage, based on at least one main-shot parameter. The system further includes an image processing unit communicatively coupled to the optical sensor and the X-ray device and configured to determine the one or more-pre-shot parameters based on the optical image. The image processing unit is further configured to determine the at least one main-shot parameter based on the pre-shot X-ray image.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

As will be described in detail hereinafter, a system and a method are disclosed for mobile X-ray imaging and in particular to a system and a method for minimizing exposure of a subject to radiation while performing optimal imaging of the subject.

As discussed herein, the term 'pre-shot X-ray image' refers to an X-ray image acquired by emitting a first X-ray beam of a first X-ray dosage towards a subject and detecting a transmitted X-ray beam attenuated by the subject. The term 'pre-shot parameters' refer to parameters used to obtain the pre-shot X-ray image. The term 'main-shot X-ray image' refers to an X-ray image acquired by emitting a second X-ray beam of a second X-ray dosage towards a subject and detecting a transmitted X-ray beam attenuated by the subject. The term 'main-shot parameter' refers to a parameter used to obtain the main-shot X-ray image. The first X-ray dosage has a relatively low dosage value compared to the second X-ray dosage having a relatively higher dosage value. Typically, the first X-ray dosage (pre-shot X-ray dosage) would be in the range of 1-15 percent of the second X-ray dosage (main-shot X-ray dosage). The term 'optical sensor' may refer to a camera, an imaging device, a depth sensor, or any other sensor configured to detect optical signals from an anatomy of interest from a subject.

Figure 1:
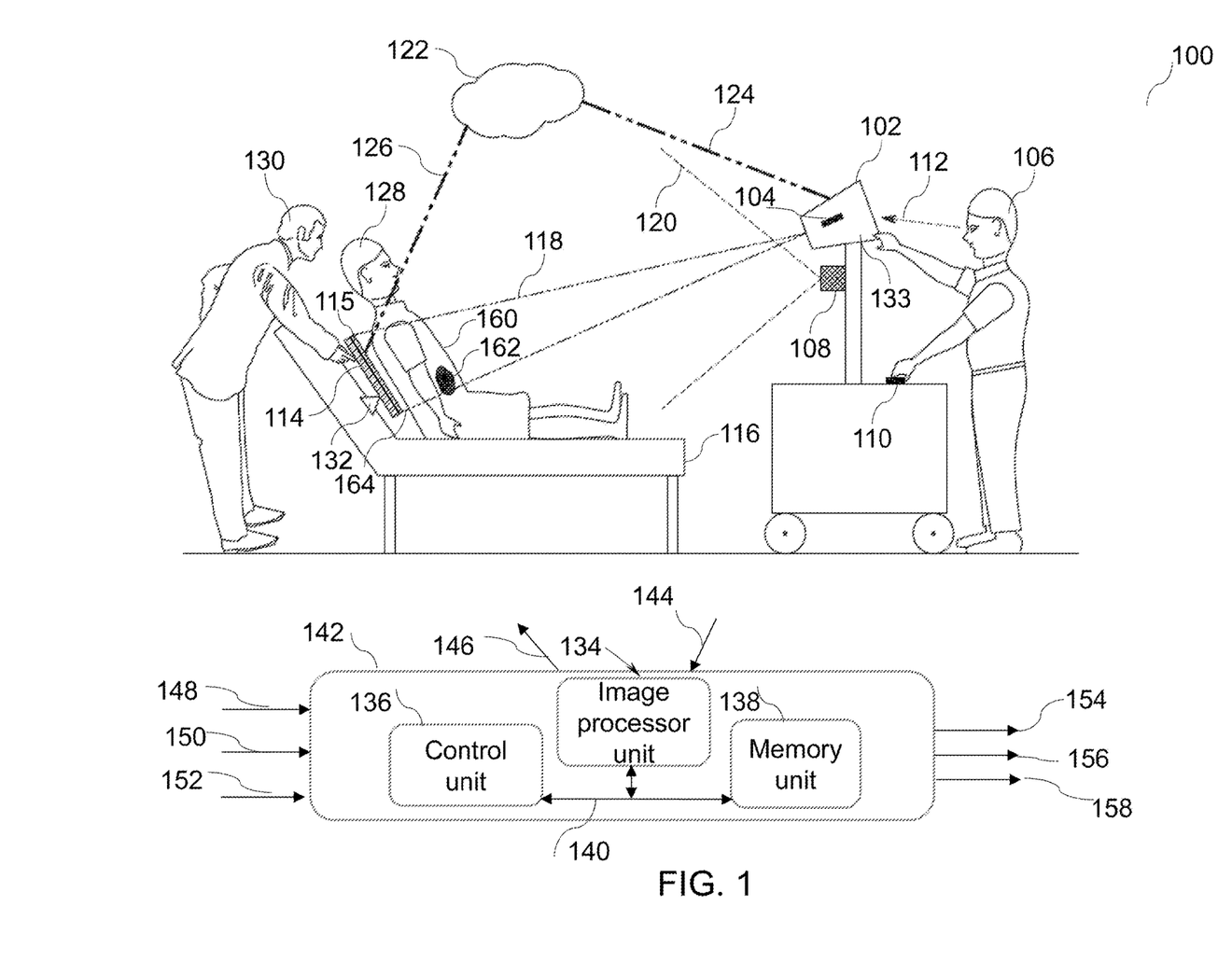
FIG. 1 is a schematic illustration of a system for performing mobile X-ray imaging of a subject in accordance with an exemplary embodiment.

FIG. 1 is a schematic illustration of a system 100 for performing mobile X-ray imaging in accordance with an exemplary embodiment. The system 100 includes a X-ray device 102 having a X-ray source 104 operated by an operator 106. The X-ray source 104 is portable and configured to emit an X-ray beam 118 towards a subject 128. In some embodiments, the system 100 may be related to imaging systems such as, but not limited to fluoroscopy imaging system and a radiology-tomography imaging system. In some embodiments, the system 100 may be a dual-energy imaging system or a triple-energy imaging (also referred to as K-edge imaging) system. The X-ray device 102 is provided with an optical sensor 108 configured to acquire an optical image 152 with reference to a field of view determined based on an optical sensor viewing angle 120. The optical sensor 108 may include a single camera, or a plurality of cameras, or a depth sensor, or a combination of cameras, depth sensors, and other types of imaging devices. In the illustrated embodiment, the optical sensor 108 has a field of view covering a region of interest 160 of the subject 128. The region of interest 160 is selected to include an anatomy 162 within the subject 128.

Additionally, the system 100 includes an X-ray detector 114 located at a predetermined position with reference to the subject 128. The X-ray detector 114 is disposed behind the subject 128 at a suitable position with reference to a field of view of the X-ray source 104. The X-ray detector 114 is configured to sense an attenuated X-ray beam 164 passing through the subject 128. The X-ray detector 114 includes an anti-scatter grid 115 having a series of alternating parallel strips of lead and a radiolucent substance such as a plastic and carbon fiber and disposed between the subject 128 and the X-ray detector 114. The anti-scatter grid 115 is configured to allow primary X-ray beam to reach the subject 128 and prevent scattered X-ray beam from reaching the subject 128 by attenuating by the lead. The anti-scatter grid when in focal alignment with the X-ray source allows maximum radiation energy to pass through the subject and reach the detector to provide a good X-ray image. The system 100 further includes a processing subsystem 142 having an image processing unit 134, a control unit 136, and a memory unit 138 communicatively coupled to each other via a communications bus 140. In the illustrated embodiment, the processing subsystem 142 is located spaced apart from the X-ray device 102. In another embodiment, the processing subsystem 142 is part of the X-ray device 102. The system 100 may also include a patient bed 116, an X-ray detector adjustment mechanism 132, and an X-ray source adjustment mechanism 133 which may be controlled by another operator 130 or by the control unit 136. The X-ray detector adjustment mechanism 132 is configured to make changes to the position, direction and other related parameters of the X-ray detector 114. The X-ray source adjustment mechanism 133 is configured to make changes to the position, direction and other related parameters of the X-ray source 104.

The processing subsystem 142 is configured to receive an input control signal 144 from the X-ray device 102 and generate an output control signal 146 to control the optical sensor 108. The input control signal 144 is representative of a parameter input by the operator 106 for controlling initiation of a scanning procedure. In one embodiment, the parameter may be a binary value indicative of a command to initiate the scanning procedure. The output control signal 146 is representative of parameters such as a field of view of the optical sensor 108 and an inclination angle for tilting the optical sensor 108 to focus towards the region of interest 160. Additionally, the output control signal 146 is also representative of a parameter to initiate an acquisition of the optical image 152 by the processing subsystem 142 from the optical sensor 108. The processing subsystem 142 is configured to receive data signal indicative of the optical image 152 from the optical sensor 108.

The processing subsystem 142 is further configured to generate an output control signal representative of one or more pre-shot parameters 154 based on processing of the optical image 152. The one or more-pre-shot parameters 154 may include subject lateral size, thickness and the habitus of the subject 128, and X-ray attenuating properties in the region of interest 160 of the subject 128. Furthermore, pre-shot parameters 154 may include geometric properties of the anatomy 162 such as size, length, circumference of the anatomy and a parameter indicating alignment of the X-ray source 104, the anatomy 162, and the X-ray detector 114. In one embodiment, the output control signal representative of the one or more-pre-shot parameters 154 is representative of a field of view and an inclination angle corresponding to the X-ray source 104. The output control signal representative of the one or more pre-shot parameters 154 also enables controlling the X-ray source 104 and initiate acquisition of a pre-shot X-ray image 148 of the region of interest 160. In one embodiment, the one or more-pre-shot parameters 154 may enable acquisition of a plurality of pre-shot X-ray images 148 corresponding to a plurality of focal spot positions. The plurality of focal spot positions corresponds to a plurality of inclination angles of the X-ray source 104 usable for emitting X-ray beam towards the subject and the detector. In one embodiment, the plurality of focal spot positions is predetermined. In some embodiments, the plurality of focal spot positions is computed based on previously acquired images.

The control unit 136 is configured to control the position of the X-ray source 104 to emit the X-ray beam 118 to the plurality of focal spot positions. In some embodiments, the output control signal representative of the one or more-pre-shot parameters 154 may be a multi-valued variable indicative of a command to initiate an acquisition of the pre-shot X-ray image 148. The processing subsystem 142 is further configured to receive an input control signal representative of the pre-shot X-ray image 148 of the region of interest 160 from the X-ray detector 114. The processing subsystem 142 is further configured to generate an output signal representative of at least one main-shot parameter 156 based on the processing of the pre-shot X-ray image 148 of the region of interest 160. Processing of the pre-shot X-ray image 148 may generate a parameter representative of attenuation of the X-ray beam 118 through the region of interest 160, and another parameter indicative of projection of the entire anatomy 162 to the X-ray detector 114. Further, the at least one main-shot parameter 156 may be representative of a correction of an orientation of the X-ray device 102 based on contents of the pre-shot X-ray image 148. In one embodiment, an optimal focal spot position is estimated as the main-shot parameter 156 based on the plurality of pre-shot X-ray images 148. The optimal focal point position may refer to a focal spot position that provide best pre-shot X-ray image among the plurality of pre-shot X-ray images. The X-ray image among the plurality of pre-shot X-ray images, corresponding to the optimal focal point position is selected as the pre-shot X-ray image. The output signal representative of the at least one main-shot parameter 156 enables controlling the X-ray source 104 and initiate acquisition of a main-shot X-ray image 158. The processing subsystem 142 is further configured to receive an input control signal representative of acquired main-shot X-ray image 150 from the X-ray device 102 and generate the main-shot X-ray image 158 using image formation techniques.

It may be noted that herein that receiving of the input control signal 144, generation of output control signal 146, generation of the one or more-pre-shot parameters 154, and generation of the at least one main-shot parameter 156 are performed specifically by the control unit 136. Further, generation of the optical image 152 based on data signal from the optical sensor 108, processing of the optical image 152 to generate the one or more-pre-shot parameters 154, processing of the pre-shot X-ray image 148 of the region of interest 160 to generate the at least one main-shot parameter 156, and generation of the main-shot X-ray image 158 of the region of interest 160 are performed by the image processing unit 134. The memory unit 138 is configured to store a plurality of scan parameters corresponding to a plurality of types of organs. In one embodiment, the scan parameters include a plurality of X-ray source parameters 124 and a plurality of X-ray detector parameters 126 of the X-ray device 102 and the X-ray detector 114 respectively. The scan parameters may be transmitted from the processing subsystem 142 to the X-ray device 102 and the X-ray detector 114 via a wired or a wireless network 122. The plurality of scan parameters may include, but is not limited to, field of view of the X-ray beam 118, orientation of the X-ray device 102 and position of the X-ray detector 114 for each type of organ. The memory unit 138 is further configured to store the optical image 152, the pre-shot X-ray image 148 and the main-shot X-ray image 150 of the region of interest 160.

Specifically, the scanning procedure is initiated by the operator 106 after the X-ray device 102 and the X-ray detector 114 are positioned with respect to the subject 128. The input control signal 144 is generated by the X-ray device 102 when a switch 110 of the X-ray device 102 is operated by the operator 106. In certain other embodiments, the input control signal 144 is generated by the X-ray device 102 when the operator 106 selects a menu item from a plurality of scanning options displayed on a display panel of the X-ray device 102. The image processing unit 134 receives the data signal representative of the optical image 152 from the optical sensor 108 and analyzes the received optical image 152 to verify presence of an image of the region of interest 160.

If the image of the region of interest 160 is present in the received optical image 152, the image processing unit 134 provides a corresponding signal to the control unit 136. The control unit 136 provides the output control signal representative of the one or more pre-shot parameters 154 to the X-ray source 104 to initiate acquisition of the pre-shot X-ray image 148. If the image of the region of interest 160 is not present in the received optical image 152, the image processing unit 134 determines one or more sensor parameters of the optical sensor 108 required for adjusting the quality of the optical image 152 based on an object recognition technique. The sensor parameters may include, but not limited to, field of view, positional information of the optical sensor 108, and distance between the subject 128 and the optical sensor 108. The control unit 136 generates an output control signal for controlling the optical sensor 108 based on field of view data provided by the image processing unit 134. The control unit 136 may also generate an output control signal representative of commands to adjust the X-ray detector 114 or the patient bed 116 based on the determined one or more sensor parameters of the optical sensor 108. After adjustments of the optical sensor 108 and/or the patient bed 116 are performed, the control unit 136 the output control signal to initiate acquisition of the optical image 152.

The image processing unit 134 is used to analyze the generated optical image 152. In one embodiment, specifically, the image processing unit 134 derives positional information of the region of interest 160 of the subject 128 from the optical image 152 using at least one of a stereo parallax technique, a 3D depth point-cloud mapping technique, and a simultaneous localization and mapping (SLAM) technique. When the stereo parallax technique is used, a pair of images corresponding to the region of interest 160 is obtained at slightly different angles. The pair of images may be used to triangulate the distance to the region of interest 160 with a higher degree of accuracy. When the 3D point-cloud mapping technique is used, a data structure representative of 3D data and amenable to provide triangulate depth information corresponding to the region of interest 160 is generated. SLAM technique is used to simultaneously localize and map the region of interest 160 with reference to the surrounding region.

Further, in one embodiment, the image processing unit 134 determines the one or more pre-shot parameters 154 based on a body size of the subject 128, habitus of the subject 128, a size and a position of the anatomy 162 within the subject 128. In one embodiment, the position of anatomy 162 may be determined based on a face detection technique, an object detection technique, or a combination thereof. The one or more-pre-shot parameters 154 may also be selected based on geometrical parameters such as, but not limited to, a distance between the X-ray source 104 and the X-ray detector 114, a position of the X-ray detector 114, and a position of a collimator of the X-ray device 102. The one or more-pre-shot parameters 154 may include pre-shot exposure parameters such as peak kilo voltage (kVp) and milli-amperes of current (mA) applied to the X-ray device 102, and time duration (T) of excitation of the X-ray device 102. The pre-shot exposure parameters are selected such that the first X-ray dosage ranging from about one percent to about fifteen percent of the second X-ray dosage is delivered to the subject 128. In a more specific embodiment, the first X-ray dosage is about ten percent of the second X-ray dosage. In one embodiment, the one or more-pre-shot parameters 154 also includes orientation of the X-ray source 104, position of the X-ray detector 114, current provided to an X-ray tube of the X-ray device 102, peak kilo voltage applied to an anode of the X-ray device 102, and the time duration for which the X-ray tube is excited.

Further, the control unit 136 provides the output control signal representative of the one or more pre-shot parameters 154 to the X-ray source 104 to initiate acquisition of the pre-shot X-ray image 148. In one embodiment, the control unit 136 adjusts the X-ray source 104 to collimate the X-ray beam 118 to the region of interest 160 based on the output control signal representative of the one or more pre-shot parameters 154. The control unit 136 may be also used to adjust the position of the X-ray detector 114 based on the output control signal representative of the one or more-pre-shot parameters 154. In some embodiments, the operator 106 may also perform the adjustments of the X-ray source 104, the X-ray detector 114, and the positioning of the subject 128 based on a visual feedback 112. Specifically, the control unit 136 controls the X-ray source 104 to emit the X-ray beam 118 having the first X-ray dosage towards the region of interest 160 of the subject 128.

Further, the image processing unit 134 processes the generated pre-shot X-ray image 148 to ascertain feasibility of acquiring the main-shot X-ray image 150. The image processing unit 134 is used to detect presence of an image of the anatomy 162 in the pre-shot X-ray image 148 based on one or more object recognition techniques. In certain embodiments, when the image of the anatomy 162 is not present in the pre-shot X-ray image 148, the control unit 136 aborts acquisition of the main-shot X-ray image 150. Alternatively, when the image of the anatomy 162 is so significantly misaligned in the pre-shot X-ray image 148 that a useful main-shot X-ray would not be obtainable, the control unit 136 aborts acquisition of the main-shot X-ray image 150.

If the presence of the image of the anatomy 162 is present in the acquired pre-shot X-ray image 148, the image processing unit 134 generates the at least one main-shot parameter 156. The main-shot parameter 156 is also dependent on misalignment of image of the anatomy 162 within the pre-shot X-ray image 148. Furthermore, the image processing unit 134 processes the plurality of pre-shot X-ray images to ascertain feasibility of acquiring the main-shot X-ray image 150. In some embodiments, the image processing unit 134 is configured to select an optimal pre-shot X-ray image among the plurality of pre-shot X-ray images 148 corresponding to an optical focal spot position of the region of interest 160. Further, the image processing unit 134 is configured to determine an image intensity value of the X-ray beam 118 received by the X-ray detector 114 based on intensity of pixel values of the optimal pre-shot X-ray image. The image processing unit 134 is further configured to compare the image intensity value of the X-ray beam 118 to a pre-determined intensity threshold value. The image processing unit 134 may be further configured to generate a control signal if the image intensity value of the X-ray beam 118 is less than the pre-determined intensity threshold value and transmit the control signal to the control unit 136. In such embodiments, the control unit 136 is configured to abort acquisition of the main-shot X-ray image 150 upon reception of the control signal. The pre-determined intensity threshold value may be provided by an operator or retrieved from a memory location. In one embodiment, the pre-determined intensity threshold value is determined based on an acceptable level of misalignment of the X-ray beam 118 with the anti-scatter grid 115. The step of retrieving stored parameter values from a memory unit is based on at least one of a view angle of the X-ray device, an attenuation of an X-ray beam by an anatomy in the region of interest of the subject, a position of the anatomy in the region of interest of the subject.

Further, the control unit 136 provides the output control signal representative of the at least one main-shot parameter 156 to the X-ray source 104 to initiate acquisition of main-shot X-ray image 150. Specifically, the control unit 136 controls an orientation of the X-ray source 104 towards the anatomy 162. Further, the control unit 136 controls the X-ray source 104 to generate the X-ray beam 118 having a second X-ray dosage greater than the first X-ray dosage to generate the main-shot X-ray image 150. Further, the image processing unit 134 receives the input control signal representative of the acquired main-shot X-ray image 150 and perform image analysis to determine presence of the image of the anatomy 162 within the acquired main-shot X-ray image 150. If the presence of the image of the anatomy 162 is present in the acquired main-shot X-ray image 150, the image processing unit 134 may generate a medical recommendation based on the acquired main-shot X-ray image 150.

It should be noted herein that the pre-shot X-ray image 148 and the main-shot X-ray image 150 may be compressed for ensuring short latency during storage, retrieval, and transmission. In one embodiment, a wireless transmission technique may be employed to transmit the pre-shot X-ray image 148 and/or the main-shot X-ray image 150 to a console. In an alternate embodiment, the processing related to acquisition and/or compression of the pre-shot X-ray image 148 and/or of the main-shot X-ray image 150 may be performed inside the X-ray detector 114, using a processor.

In one embodiment, the control unit 136 includes at least one of a general-purpose computer, a graphics processing unit (GPU), a digital signal processor, and a controller. In other embodiments, the control unit 136 includes a customized processor element such as, but not limited to, an application-specific integrated circuit (ASIC) and a field-programmable gate array (FPGA). In some embodiments, the control unit 136 may also perform one or more functions of the image processing unit 134. The control unit 136 may include more than one processor co-operatively working with each other for performing intended functionalities. The control unit 136 is further configured to store and retrieve contents into and from the memory unit 138. In one embodiment, the control unit 136 is configured to initiate and control the functionality of the image processing unit 134.

In some embodiments, the control unit 136 may be communicatively coupled with at least one of a keyboard, a mouse, and any other input device and configured to receive commands and/or parameters from the operator 106 via a console. When the control unit 136 is configured to perform the functionality of the image processing unit 134, the control unit 136 is programmed to process the optical image 152 of the region of interest 160 to derive the one or more pre-shot parameters 154, process the pre-shot X-ray image 148 of the region of interest 160 to derive the at least one main-shot parameter 156, and perform registration of images among other image processing related functionalities.

In one embodiment, the memory unit 138 is a random-access memory (RAM), a read only memory (ROM), a flash memory, or any other type of computer readable memory accessible by at least one of the image processing unit 134 and the control unit 136. Also, in certain embodiments, the memory unit 138 may be a non-transitory computer readable medium encoded with a program having a plurality of instructions to instruct at least one of the image processing unit 134 and the control unit 136 to perform a sequence of steps to generate the main-shot X-ray image 150 of the region of interest 160. Specifically, the instructions may enable the optical sensor 108 to generate the optical image 152 of the region of interest 160, the X-ray source 104 to generate either the pre-shot X-ray image 148 or the main-shot X-ray image 150 of the region of interest 160, the image processing unit 134 to generate the one or more-pre-shot parameters 154 corresponding to the region of interest 160 in the subject 128 based on the optical image 152 of the region of interest 160 obtained from an optical sensor 108. The instructions further enable the processing unit 134 to control an X-ray device 102 to generate a pre-shot X-ray image 148 using a first X-ray dosage, based on the one or more-pre-shot parameters. The instructions also enable the processing unit 134 to determine at least one main-shot parameter 156 based on the pre-shot X-ray image 148. The instructions may also enable the control unit 136 to initiate the acquisition of the pre-shot X-ray image 148 of the region of interest 160, the main-shot X-ray image 150 of the region of interest 160, and perform other control actions. The memory unit 138 is configured to store the acquired pre-shot X-ray image 148, the main-shot X-ray image 150, and the optical image 152 of the region of interest 160. The instructions further enable the processing unit 134 to control the X-ray device 102 to generate a main-shot X-ray image 150 using a second X-ray dosage greater than the first X-ray dosage, based on the at least one main-shot parameter.

Figure 2:
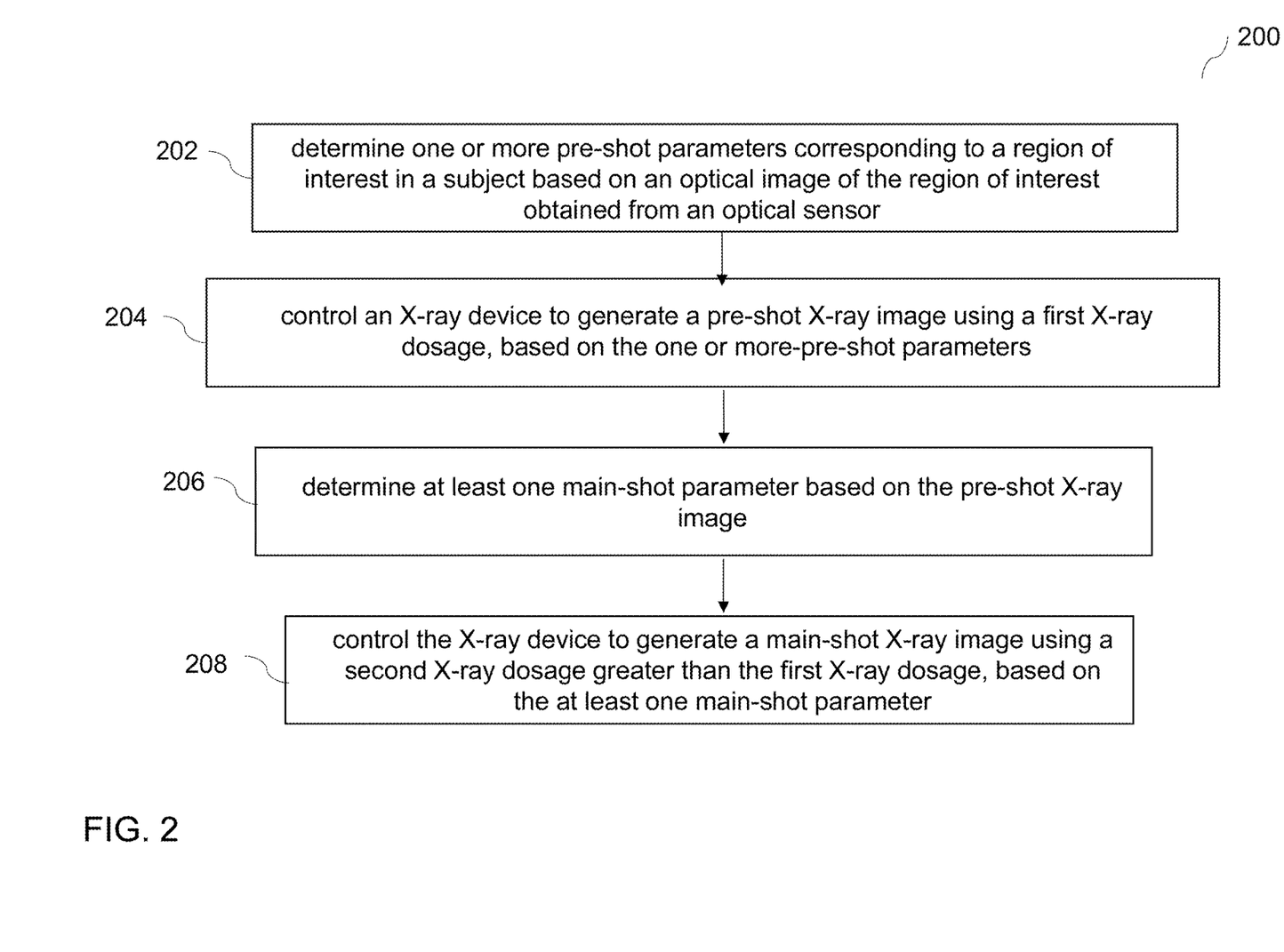
FIG. 2 is a flow chart illustrating a method for performing mobile X-ray imaging in accordance with an exemplary embodiment.

FIG. 2 is a flow chart 200 of a method for mobile X-ray imaging in accordance with an exemplary embodiment of FIG. 1. The method 200 includes determining the one or more-pre-shot parameters 154 based on the optical image 152 of the region of interest 160 of the subject 128 obtained from the optical sensor 108 at step 202. The one or more-pre-shot parameters 154 are determined by the image processing unit 134. The optical image is obtained by the optical sensor 108 such as, but not limited to, a camera or a depth sensor. In one embodiment, more than one optical sensor 108 may be used simultaneously to acquire a plurality of optical images. In some embodiments, the optical sensor 108 may be controlled to acquire the optical image 152 of the region of interest 160 of the subject 128 based on an object recognition technique. In one embodiment, a three-dimensional positional information of the anatomy 162 within the region of interest 160 may be obtained based on at least one of a stereo parallax technique, a three-dimensional depth point-cloud mapping technique, and a simultaneous localization and mapping (SLAM) technique applied to the optical image 152. In another embodiment, the three-dimensional positional information of the anatomy 162 may be obtained based on a plurality of optical images obtained from the plurality of optical sensors 108. In yet another embodiment, the three-dimensional position information of the anatomy 162 within region of interest 160 of the subject 128 may be obtained based on depth information corresponding to the region of interest 160 and the optical image 152 of the region of interest 160 of the subject 128 detected by the optical sensor 108.

The method 200 further includes controlling the X-ray source 104 to generate the pre-shot X-ray image 148 based on the output control signal representative of the one or more-pre-shot parameters 154 at step 204. The step of controlling the X-ray source 104 is performed by the control unit 136. The pre-shot X-ray image 148 is obtained by emitting the X-ray beam 118 having a first X-ray dosage towards the region of interest 160 of the subject 128. In one embodiment, the method 200 further includes analyzing the pre-shot X-ray image 148 to verify presence of the image of the anatomy 162. If the image of the anatomy 162 is not present in the pre-shot X-ray image 148, the method 200 further includes a step of aborting acquisition of the main-shot X-ray image 150. Further, the method 200 may include a step of determining focal alignment between the X-ray source 104 and the anti-scatter grid 115. If the focal alignment between the X-ray source 104 and the anti-scatter grid 115 is not present, the method 200 includes a step to abort the acquisition of the main-shot X-ray image.

The method 200 also includes determining the at least one main-shot parameter 156 based on the pre-shot X-ray image 148 at step 206. The at least one main-shot parameter 156 is determined by the image processing unit 134. In one embodiment, determining the at least one main-shot parameter 156 includes selecting a view angle of the X-ray device 102 from a configurational atlas catalog. The configurational atlas catalog includes a comprehensive listing of the scan parameters corresponding to a plurality of X-ray views. In another embodiment, the step of determining the at least one main-shot parameter 156 includes registering the pre-shot X-ray image 148 with several reference anatomical images stored in the memory unit 138. The memory unit 138 is used to store scan parameters corresponding to each of the reference anatomical images. A registered reference image closely matching with the pre-shot X-ray image 148 is determined as an output of the registration process. In one embodiment, image parameters corresponding to the registered reference image is determined as the at least one main-shot parameter 156. In another embodiment, the step of determining the at least one main-shot parameter 156 includes estimating attenuation of the X-ray beam 118 by the anatomy 162 of the subject 128. In some embodiments, the at least one main-shot parameter 156 corresponding to at least one of a view angle of the X-ray source 104, attenuation of the X-ray beam 118 by the anatomy 162, a position of the anatomy 162 may be stored within a memory location of the memory unit 138. The step of determining the at least one main-shot parameter 156 includes retrieving the at least one stored parameter from the memory location of the memory unit 138 based on at least one of the view angle of the X-ray source 104, the attenuation of the X-ray beam 118 by the anatomy 162, and the position of the anatomy 162. In one embodiment, at least one of the main-shot parameter 156 corresponding to an anatomy of a subject is determined by retrieving stored parameters corresponding to an image stored in an image database. The stored image may be selected based on patient information, the anatomy, medical condition of the subject or other scanning specific information. In a specific embodiment, the stored image may correspond to the same anatomy of the same subject. The stored image may also be selected based on patient orientation or other geometric parameters of the imaging system. The patient identification information, patient orientation information of the subject under examination or geometric parameters of the imaging system may be determined from techniques such as, but not limited to, face recognition technique and object recognition technique. Further, patient orientation information or other imaging geometrical parameters of the subject are compared with the stored images to select a matching image.

At step 208, the method 200 includes controlling the X-ray source 104 to generate the main-shot X-ray image 150 based on the output control signal representative of the at least one main-shot parameter 156. The step of controlling the X-ray source 104 to generate the main-shot X-ray image 150 is performed by the control unit 136. Specifically, the main-shot X-ray image 150 is obtained by emitting the X-ray beam 118 having a second X-ray dosage greater than the first x-ray dosage, towards the region of interest 162 of the subject 128 and then detecting a transmitted X-ray beam 164 by the anatomy 162. It should be noted herein that the X-ray dosage is controlled by regulating an intensity of the X-ray beam 118.

Figure 3:
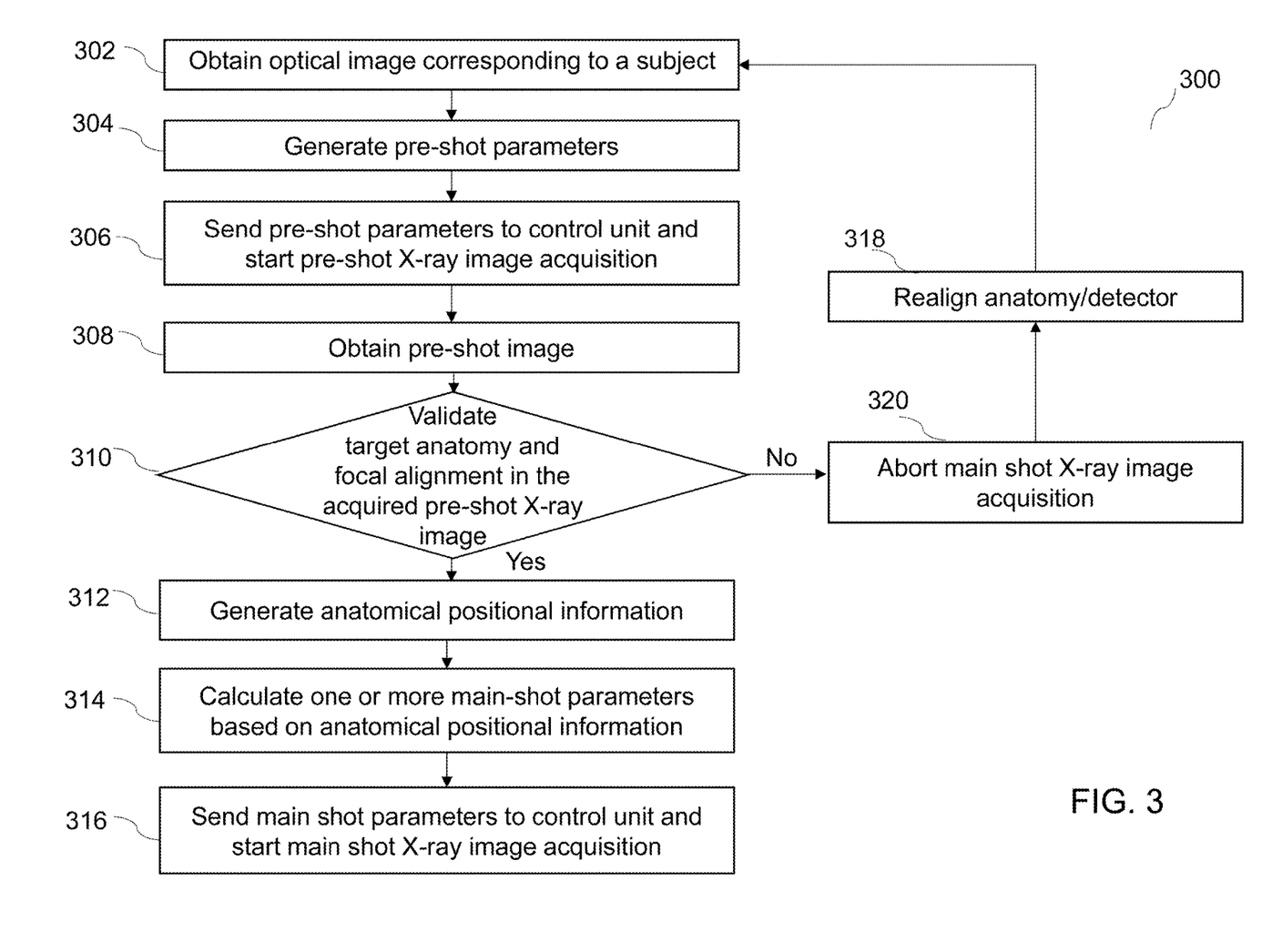
FIG. 3 is a flow chart illustrating a work-flow for performing mobile X-ray imaging of a subject using the system of FIG. 1 in accordance with an exemplary embodiment.

FIG. 3 is a flow chart illustrating work-flow 300 for mobile X-ray imaging using the system 100 of FIG. 1 in accordance with an exemplary embodiment. The work-flow 300 includes obtaining the optical image 152 of the region of interest 160 of the subject 128 at step 302. The work-flow 300 further includes generating the one or more-pre-shot parameters 154 based on the obtained optical image 152 at step 304. The work-flow 300 further includes sending the output control signal representative of the one or more-pre-shot parameters 154 from the control unit 136 to the X-ray source 104 to start acquisition of the pre-shot X-ray image 148 at step 306. At step 308, image acquisition is performed to obtain the pre-shot X-ray image 148. The work-flow 300 may include realigning at least one of the anatomy 162, the X-ray source 104, and the X-ray detector 114 based on the output control signal representative of the one or more-pre-shot parameters 154. In some embodiments, at least one of a direction of motion of the X-ray source 104, a direction of motion of the anatomy 162, and a direction of movement of the X-ray detector 114 required to achieve a mutual projective alignment, is calculated by the control unit 136. In another embodiment, the control unit 136 may automatically actuate the X-ray detector 114, the X-ray source 104, and provide guidance to position the subject 160 to achieve the projective alignment. The work-flow 200 further includes validating presence of an image of the anatomy 162 in the acquired pre-shot X-ray image 148 at step 310. Further, focal alignment between the X-ray source 104 and the anti-scatter grid 115 may also be validated at step 310. If the validation is successful, acquisition of the main-shot X-ray image 150 is initiated. At step 312, position information of the anatomy 162 is generated based on the pre-shot X-ray image 148. The position information of the anatomy 162 is representative of 3D position information of the anatomy 162 in the region of interest 160 of the subject 128. The work-flow 200 further includes determining the at least one main-shot parameter 156 based on the position information of the anatomy 162 at step 314. The main-shot parameter 156 is also based on extent of misalignment of image of the anatomy within the boundary of the pre-shot X-ray image. The output control signal representative of the at least one main-shot parameter 156 is sent from the control unit 136 to the X-ray source 104 to initiate the acquisition of the main-shot X-ray image 150 at step 316. Alternatively, at step 310, if the image of the anatomy 162 is not present in the acquired pre-shot X-ray image 148 or if the focal alignment between the X-ray source 104 and the anti-scatter grid 115 is not present, the acquisition of a main-shot X-ray image is aborted at step 320.

In one embodiment, a plurality of image metrics is derived based on the pre-shot X-ray image 148, optical sensor data, anatomy model data, and prior patient imaging data from a picture archiving and communication system (PACS) database. The image metrics are representative of a field of view (FOV) of the X-ray source 104 and may be derived from meta data corresponding to an X-ray image. The plurality of image metrics may be used to optimize image geometry, X-ray source parameters, and X-ray beam collimation.

In accordance with the embodiments disclosed herein, the exemplary optical imaging technique includes determining one or more pre-shot parameters. The determination of the one or more pre-shot parameters facilitates acquisition of a pre-shot X-ray image using a low dosage X-ray beam that enables to precisely adjust the position of a subject with reference to the mobile X-ray imaging system to acquire a good quality main-shot X-ray image. The at least one main-shot parameter required to acquire the main-shot X-ray image is determined based on the pre-shot X-ray image. If an image of an anatomy of interest is not present in the pre-shot X-ray image, the acquisition of the main-shot X-ray image can be aborted. Hence, unwanted exposure of a subject to an X-ray beam having a high dosage can be avoided.

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the specification is not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the specification may include only some of the described embodiments. Accordingly, the specification is not to be seen as limited by the foregoing description, but is only limited by the scope of the appended claims.

The invention claimed is:

1. A method comprising:
   determining one or more pre-shot parameters corresponding to a region of interest in a subject based on an optical image of the region of interest obtained from an optical sensor;
   controlling an X-ray device to generate a pre-shot X-ray image using a first X-ray dosage, based on the one or more pre-shot parameters, wherein generating the pre-shot X-ray image comprises:
      generating a plurality of pre-shot X-ray images corresponding to a plurality of focal spot positions, wherein the plurality of focal spot positions corresponds to a plurality of inclination angles of an X-ray source of the X-ray device;
      determining an optimal focal spot position among the plurality of focal spot positions based on the plurality of pre-shot X-ray images; and
      selecting the pre-shot X-ray image among the plurality of pre-shot X-ray images corresponding to the optimal focal spot position;
   analyzing the pre-shot X-ray image to verify presence of an image of an anatomy of the subject in the pre-shot X-ray image;
   determining at least one main-shot parameter based on the pre-shot X-ray image;
   when the image of the anatomy of the subject is present in the pre-shot X-ray image, controlling the X-ray device to generate the main-shot X-ray image using a second X-ray dosage greater than the first X-ray dosage, based on the at least one main-shot parameter; and
   aborting acquisition of the main-shot X-ray image when the image of the anatomy of the subject is not present in the pre-shot X-ray image.

2. The method of claim 1, further comprising:
   selecting an optimal pre-shot X-ray image among the plurality of pre-shot X-ray images corresponding to the optimal focal spot position;
   determining an image intensity value corresponding to the optimal pre-shot X-ray image based on intensity of pixel values of the optimal pre-shot X-ray image;
   comparing the image intensity value with a pre-determined intensity threshold value; and
   aborting acquisition of the main-shot X-ray image if the image intensity value is less than the pre-determined intensity threshold value.

3. The method of claim 1, wherein determining the one or more-pre-shot parameters comprises deriving three-dimensional positional information of the region of interest in the subject based on at least one of a stereo parallax technique, a three-dimensional depth point-cloud mapping technique, and a simultaneous localization and mapping (SLAM) technique.

4. The method of claim 3, wherein the three-dimensional position information of the region of interest in the subject is derived based on a depth information corresponding to the region of interest detected by a depth sensor and the optical image of the region of interest in the subject.

5. The method of claim 1, wherein determining the at least one main-shot parameter comprises selecting a view angle of the X-ray device from a configurational atlas catalog.

6. The method of claim 1, wherein determining the at least one main-shot parameter comprises registering the pre-shot X-ray image with a reference anatomical image.

7. The method of claim 1, wherein determining the at least one main-shot parameter comprises estimating an attenuation of an X-ray beam generated from the X-ray device, by the anatomy in the region of interest of the subject.

8. The method of claim 1, wherein determining the at least one main-shot parameter comprises retrieving stored parameter values from a memory unit based on at least one of a view angle of the X-ray device, an attenuation of an X-ray beam by the anatomy in the region of interest of the subject, a position of the anatomy in the region of interest of the subject.

9. The method of claim 1, wherein determining the at least one main-shot parameter comprises determining a position of the anatomy in the region of interest of the subject based on at least one of a face detection technique and an object detection technique.

10. The method of claim 1, wherein the one or more pre-shot parameters comprise a lateral size of the subject, a thickness of a subject, a habitus of the subject, X-ray attenuating properties in the region of interest of the subject, geometric properties of the anatomy, and a parameter indicating alignment of an X-ray source of the X-ray device, the anatomy, and an X-ray detector of the X-ray device.

11. A system comprising:
an optical sensor configured to obtain an optical image of a region of interest in a subject;
an X-ray device configured to:
generate a pre-shot X-ray image, using a first X-ray dosage, based on one or more pre-shot parameters;
generate a main-shot X-ray image, using a second X-ray dosage greater than the first X-ray dosage, based on at least one main-shot parameter; and
an image processing unit communicatively coupled to the optical sensor and the X-ray device, wherein the image processing unit is configured to:
determine the one or more pre-shot parameters based on the optical image;
determine the at least one main-shot parameter based on the pre-shot X-ray image;
analyze the pre-shot X-ray image to verify presence of an image of an anatomy of the subject in the pre-shot X-ray image; and
abort acquisition of the main-shot X-ray image when the image of the anatomy of the subject is not present in the pre-shot X-ray image; and
wherein the image processing unit is further configured to:
generate a plurality of pre-shot X-ray images, by the X-ray device, corresponding to a plurality of focal spot positions, wherein the plurality of focal spot positions corresponds to a plurality of inclination angles of an X-ray source of the X-ray device; and
estimate an optimal focal spot position, by the image processing unit, based on the plurality of pre-shot X-ray images.

12. The system of claim 11, wherein the optical sensor comprises at least one of a camera and a depth sensor.

13. The system of claim 11, wherein the image processing unit is further configured to:
select an optimal pre-shot X-ray image among the plurality of pre-shot X-ray images corresponding to the optimal focal spot position;
determine an image intensity value corresponding to the optimal pre-shot X-ray image based on intensity values of pixels of the optimal pre-shot X-ray image;
compare the image intensity value with a pre-determined intensity threshold value; and
abort acquisition of the main-shot X-ray image if the image intensity value is less than the pre-determined intensity threshold value.

14. The system of claim 11, wherein the image processing unit is configured to generate the one or more-pre-shot parameters by deriving three-dimensional positional information of the anatomy of the subject based on at least one of a stereo parallax technique, a three-dimensional depth point-cloud mapping technique, and a simultaneous localization and mapping (SLAM) technique.

15. The system of claim 11, wherein the image processing unit is configured to determine the at least one main-shot parameter by selecting a view angle of the X-ray device from a configurational atlas catalog.

16. The system of claim 11, wherein the image processing unit is configured to register the pre-shot X-ray image with a reference anatomical image.

17. The system of claim 11, wherein the image processing unit is configured to determine the at least one main-shot parameter by estimating attenuation of an X-ray beam generated from the X-ray device, by the anatomy in the region of interest of the subject.

18. The system of claim 11, wherein the one or more pre-shot parameters comprise a lateral size of the subject, a thickness of a subject, a habitus of the subject, X-ray attenuating properties in the region of interest of the subject, geometric properties of the anatomy, and a parameter indicating alignment of an X-ray source of the X-ray device, the anatomy, and an X-ray detector of the X-ray device.

* * * * *